US008655457B2

(12) United States Patent
DiGiore et al.

(10) Patent No.: US 8,655,457 B2
(45) Date of Patent: *Feb. 18, 2014

(54) PADDLE LEAD CONFIGURATIONS FOR ELECTRICAL STIMULATION SYSTEMS AND METHODS OF MAKING AND USING

(71) Applicant: Boston Scientific Neuromodulation Corporation, Valencia, CA (US)

(72) Inventors: Andrew DiGiore, San Francisco, CA (US); Greg Baldwin, Seattle, WA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/947,731

(22) Filed: Jul. 22, 2013

(65) Prior Publication Data

US 2013/0304173 A1  Nov. 14, 2013

Related U.S. Application Data

(60) Continuation of application No. 13/570,059, filed on Aug. 8, 2012, now Pat. No. 8,494,653, which is a division of application No. 12/018,397, filed on Jan. 23, 2008, now Pat. No. 8,260,434.

(51) Int. Cl.
*A61N 1/00* (2006.01)
*A61B 5/04* (2006.01)
(52) U.S. Cl.
USPC ............................ 607/116; 607/115; 600/393
(58) Field of Classification Search
USPC .................................. 607/115–116; 600/393
See application file for complete search history.

(56) References Cited

U.S. PATENT DOCUMENTS

| 6,181,969 | B1 | 1/2001 | Gord |
| 6,205,361 | B1 | 3/2001 | Kuzma et al. |
| 6,516,227 | B1 | 2/2003 | Meadows et al. |
| 6,553,264 | B2 | 4/2003 | Redko et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 6,895,280 | B2 | 5/2005 | Meadows et al. |
| 6,999,820 | B2 | 2/2006 | Jordan |
| 7,047,081 | B2 | 5/2006 | Kuzma |
| 7,107,104 | B2 | 9/2006 | Keravel et al. |

(Continued)

FOREIGN PATENT DOCUMENTS

| WO | 2006113593 A2 | 10/2006 |
| WO | 2006133443 A2 | 12/2006 |

(Continued)

OTHER PUBLICATIONS

U.S. Appl. No. 12/018,397, Official Communication mailed Dec. 24, 2009.

(Continued)

*Primary Examiner* — Nicole F Lavert
(74) *Attorney, Agent, or Firm* — Frommer Lawrence & Haug LLP; Bruce E. Black

(57) ABSTRACT

A paddle lead includes a paddle body with a plurality of electrodes disposed on the paddle body. The plurality of electrodes includes a first electrode and a second electrode. The first electrode and the second electrode are disposed laterally around the circumference of the paddle body. At least one connecting wire is disposed on, or within, the paddle body to electrically couple the first electrode and the second electrode.

20 Claims, 7 Drawing Sheets

(56) References Cited

U.S. PATENT DOCUMENTS

| | | |
|---|---|---|
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,204,607 B2 | 6/2012 | Rooney et al. |
| 8,364,278 B2 | 1/2013 | Pianca et al. |
| 2003/0236562 A1 | 12/2003 | Kuzma |
| 2004/0015221 A1 | 1/2004 | Kuzma |
| 2004/0059392 A1 | 3/2004 | Parramon et al. |
| 2005/0246004 A1 | 11/2005 | Cameron et al. |
| 2007/0021801 A1 | 1/2007 | Heruth et al. |
| 2007/0060991 A1 | 3/2007 | North et al. |
| 2007/0073353 A1 | 3/2007 | Rooney et al. |
| 2007/0073356 A1 | 3/2007 | Rooney et al. |
| 2007/0073357 A1 | 3/2007 | Rooney et al. |
| 2007/0118196 A1 | 5/2007 | Rooney et al. |
| 2007/0150034 A1 | 6/2007 | Rooney et al. |
| 2007/0150036 A1 | 6/2007 | Anderson |
| 2007/0179579 A1 | 8/2007 | Feler et al. |
| 2007/0203537 A1 | 8/2007 | Goetz et al. |
| 2007/0203538 A1 | 8/2007 | Stone et al. |
| 2007/0203540 A1 | 8/2007 | Goetz et al. |
| 2007/0203541 A1 | 8/2007 | Goetz et al. |
| 2007/0203545 A1 | 8/2007 | Stone et al. |
| 2008/0140168 A1 | 6/2008 | Walter et al. |
| 2010/0070010 A1 | 3/2010 | Simpson |

FOREIGN PATENT DOCUMENTS

| | | |
|---|---|---|
| WO | 2006133444 A2 | 12/2006 |
| WO | 2006133445 A2 | 12/2006 |
| WO | 2006135751 A2 | 12/2006 |
| WO | 2006135753 A1 | 12/2006 |
| WO | 2006135766 A2 | 12/2006 |
| WO | 2006135791 A2 | 12/2006 |
| WO | 2006135792 A1 | 12/2006 |
| WO | 2007097873 A1 | 6/2007 |
| WO | 2007087626 A2 | 8/2007 |
| WO | 2007097858 A1 | 8/2007 |
| WO | 2007097859 A1 | 8/2007 |
| WO | 2007097860 A1 | 8/2007 |
| WO | 2007097861 A1 | 8/2007 |
| WO | 2007097869 A1 | 8/2007 |
| WO | 2007097870 A1 | 8/2007 |
| WO | 2007097872 A1 | 8/2007 |
| WO | 2007100427 A1 | 9/2007 |
| WO | 2007100428 A1 | 9/2007 |
| WO | 2007101999 A2 | 9/2007 |

OTHER PUBLICATIONS

U.S. Appl. No. 12/018,397, Official Communication mailed Oct. 26, 2010.

U.S. Appl. No. 13/570,059, Official Communication mailed Jan. 14, 2013.

PADDLE LEAD CONFIGURATIONS FOR ELECTRICAL STIMULATION SYSTEMS AND METHODS OF MAKING AND USING

CROSS-REFERENCE TO RELATED APPLICATIONS

This patent application is continuation of U.S. patent application Ser. No. 13/570,059 filed Aug. 8, 2012, now U.S. Pat. No. 8,494,653, which is a divisional of U.S. patent application Ser. No. 12/018,397 filed on Jan. 23, 2008, now U.S. Pat. No. 8,260,434, all of which are incorporated herein by reference.

FIELD

The present invention is directed to the area of implantable electrical stimulation systems and methods of making and using the systems. The present invention is also directed to implantable electrical stimulation systems that include a paddle lead with an array of electrodes disposed on the paddle lead, as well as methods of making and using the systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a paddle lead includes a paddle body with a plurality of electrodes disposed on the paddle body. The plurality of electrodes includes a first electrode and a second electrode. The first electrode and the second electrode are disposed laterally around the circumference of the paddle body. At least one connecting wire is disposed on, or within, the paddle body to electrically couple the first electrode and the second electrode.

In another embodiment, a paddle lead includes a lead body for coupling the paddle lead to one or more external devices. The paddle lead also includes a paddle body distal to the lead body. The paddle body includes a plurality of electrodes disposed on the paddle body. The plurality of electrodes forms at least one lateral loop around the circumference of the paddle body.

Yet another embodiment is a method of using a paddle lead. The method includes implanting a paddle lead into a body. The paddle lead includes a paddle body and a plurality of electrodes disposed on the paddle body. The paddle lead also includes a plurality of electrodes, including a first electrode and a second electrode. The first electrode and the second electrode are disposed laterally around the circumference of the paddle body. The paddle lead further includes at least one connecting wire disposed on, or within, the paddle body to electrically couple the first electrode and the second electrode. The method also includes coupling the paddle lead to a control module and stimulating tissue near the paddle lead using two or more of the electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems that include a paddle lead with an array of electrodes disposed on the paddle lead, as well as methods of making and using the systems.

Suitable implantable electrical stimulation systems include, but are not limited to, an electrode lead with one or more electrodes disposed on a distal end of the lead and one or more terminals disposed on a proximal end of the lead. Electrodes leads include, for example, paddle leads. Examples of stimulation systems with electrode leads are found in, for example, U.S. Pat. Nos. 6,181,969; 6,516,227; 6,609,029; 6,609,032; and 6,741,892; 7,244,150; 7,672,734; 7,761,165; 7,949,395; 7,974,706; and 8,175,710; and U.S. Patent Application Publication Nos. 2005/0165465; and 2007/0150036, all of which are incorporated by reference.

Figure 1:
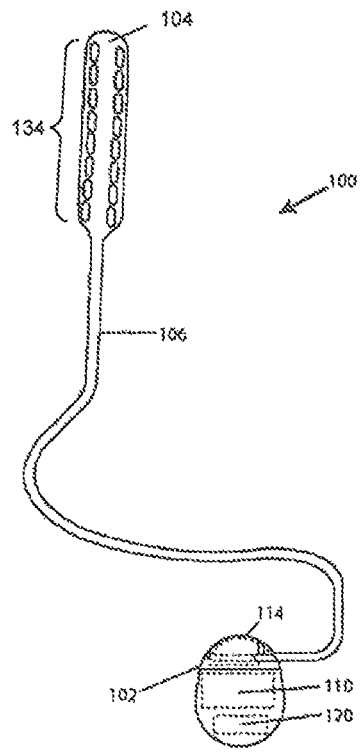
FIG. 1 is a schematic view of one embodiment of an electrical stimulation system, according to the invention.

FIG. 1 illustrates schematically one embodiment of a stimulation system 100. The stimulation system includes a control module (e.g., a stimulator or pulse generator) 102, a paddle body 104, and at least one lead body 106 coupling the control module to the paddle body. The paddle body 104 and the lead body 106 form a paddle lead. The paddle body 104 typically includes an array of electrodes 134. The control module 102 typically includes an electronic subassembly 110 and optional power source 120 disposed in a sealed housing 114. The control module 102 typically includes a port (not shown) into which the proximal end of the lead body 106 can be plugged to make an electrical connection via connective contacts in the control module and contact terminals on the lead body. It will be understood that the system for stimulation can include more, fewer, or different components including those configurations disclosed in the stimulation system references cited herein. For example, one or more lead extensions (not shown in FIG. 1) can be disposed between the control module and the paddle body to extend the distance between the control module and the paddle body.

The stimulation system or components of the stimulation system, including one or more of the lead body 106, the paddle body 104, and the control module 102, are typically implanted into the body. The stimulation system can be used for a variety of applications including, but not limited to, brain stimulation, neural stimulation, spinal cord stimulation, muscle stimulation, and the like.

The electrodes 134 can be made using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, twenty, twenty-four, twenty-eight, thirty-two, thirty-six, or more electrodes 134. As will be recognized, other numbers of electrodes 134 may also be used.

The electrodes of the paddle body 104 or lead body 106 are typically disposed in a non-conductive, biocompatible material including, for example, silicone, polyurethane, polyetheretherketone (PEEK), epoxy, and the like or combinations thereof. The paddle body 104 and lead body 106 may be formed in the desired shape by any process including, for example, molding (including injection molding), casting, and the like. The non-conductive material typically extends from the distal end of the lead to the proximal end. The non-conductive, biocompatible material of the paddle body 104 and the lead body 106 may be the same or different. The paddle body 104 and lead body 106 may be a unitary structure or can be formed as two separate structures that are permanently or detachably coupled together.

Contact terminals (not shown in FIG. 1) are typically disposed at the proximal end of the lead for connection to corresponding conductive contacts in the control module 102 (or to conductive contacts on a lead extension). Conductive wires (not shown in FIG. 1) extend from the contact terminals to the electrodes 134. Typically, one or more electrodes are electrically connected to a contact. In some embodiments, each contact terminal is only connected to one electrode. The conductive wires may be embedded in the non-conductive material of the lead or can be disposed in one or more lumens extending along the lead. In some embodiments, there is an individual lumen for each conductive wire. In other embodiments, two or more conductive wires may extend through a lumen. There may also be one or more lumens that open at, or near, the distal end of the lead, for example, for infusion of drugs or medication into the side of implantation of the paddle body.

Figure 2A:
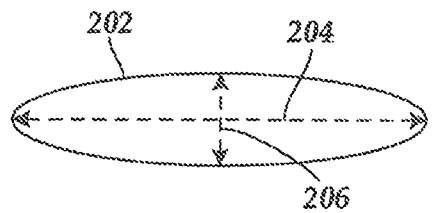
FIG. 2A is a schematic cross-sectional view of one embodiment of a paddle body for use in an electrical stimulation system, according to the invention.
Figure 2B:
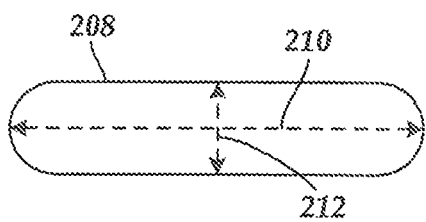
FIG. 2B is a schematic cross-sectional view of another embodiment of a paddle body for use in an electrical stimulation system, according to the invention.

FIG. 2A is a schematic cross-sectional view of one embodiment of a paddle body for use in an electrical stimulation system, according to the invention. In at least some embodiments, a paddle body 202 can have an ellipse-like cross-section with a major axis 204, indicated in FIG. 2A by a two-headed dashed arrow, and a minor axis 206, indicated in FIG. 2A by a two-headed dashed arrow orthogonal to the major axis 204. The length of the major axis 204 is greater than the length of the minor axis 206. The major axis 204 is typically longer than the minor axis 206. For example, the major axis 204 can be at least four times the length of the minor axis 206, at least five times the length of the minor axis 206, at least six times the length of the minor axis 206, at least eight times the length of the minor axis 206, at least ten times the length of the minor axis 206. As will be recognized, other relative lengths of the axes 204 and 206 may also be used. FIG. 2B is a schematic cross-sectional view of another embodiment of a paddle body for use in an electrical stimulation system, according to the invention. In other embodiments, a paddle body 208 can have a rounded-edged-rectangular-like cross-section with a major axis 210 and a minor axis 212 orthogonal to the major axis 210 and with a length that is less than the length of the major axis 210.

Figure 3:
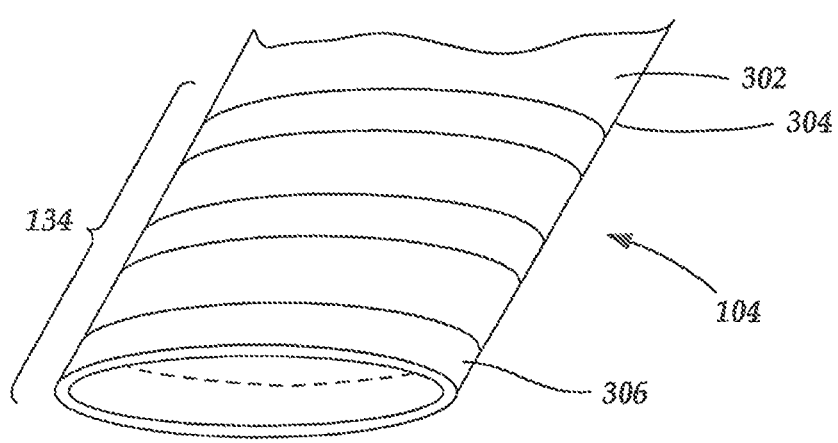
FIG. 3 is a schematic cross-sectional/perspective view of one embodiment of a paddle body for use in an electrical stimulation system, according to the invention.

FIG. 3 is a schematic cross-sectional/perspective view of one embodiment of a paddle body for use in an electrical stimulation system, according to the invention. The paddle body 104 includes two opposing major surfaces: an anterior surface 302; and an inferior surface 304. In one embodiment, the widths of the anterior surface 302 and the inferior surface 304 are determined, at least in part, by the length of the major axis (204 in FIG. 2). An array of electrodes 134 includes a plurality of electrodes, such as electrode 306, and is disposed on both the anterior surface 302 and the inferior surface 304. Each electrode shown in FIG. 3 is a unitary structure and forms a continuous lateral loop around the circumference of the paddle body 104.

In at least some embodiments, electrodes are coupled electrically to one or more conductive wires that extend from the paddle body to one or more contact terminals on a proximal end of the lead. As discussed above, the conductive wires may be embedded in the non-conductive material of the lead or can be disposed in one or more lumens extending along the lead. In some embodiments, there is an individual lumen for each conductive wire. In other embodiments, two or more conductive wires may extend through a lumen.

One advantage of the two-sided electrode arrangement on the paddle body shown in FIG. 3 over conventional one-sided electrode arrangements on conventional paddle bodies is that, with a two-sided electrode arrangement, a lead may be implanted without regard to which side of the corresponding paddle body is facing anteriorly in the body of an implantee. Thus, a health care professional implanting a stimulation system may perform the implantation with fewer concerns about paddle body orientation. Another advantage of the paddle arrangement of this embodiment is that simultaneous multidirectional stimulation may be achieved, if desired. Multidirectional stimulation may provide a number of therapeutic benefits, such as providing relief of peripheral pain. In some body regions, such as peripheral regions, a paddle lead may be more tolerated than a percutaneous lead. Thus, the paddle arrangement of this embodiment allows for the use of a paddle lead, which is typically more tolerated than a percutaneous lead, while also providing multidirectional stimulation.

It may be desirable to increase the flexibility of a paddle body. Increased flexibility may facilitate implantation of a paddle body by increasing maneuverability. One method of increasing flexibility is to substitute a unitary electrode forming a lateral loop around the periphery of a paddle body with a plurality of electrically-coupled electrodes forming a lateral loop around the periphery of a paddle body. The electrodes forming the lateral loop may be electrically coupled together by connecting wires disposed around the periphery of a paddle body or inside the paddle body. In at least some embodiments, connecting wires for lateral loops electrically coupled together by connecting wires disposed around the periphery of a paddle body are actually just below the surface of the paddle body and do not contact patient tissue.

Figure 4A:
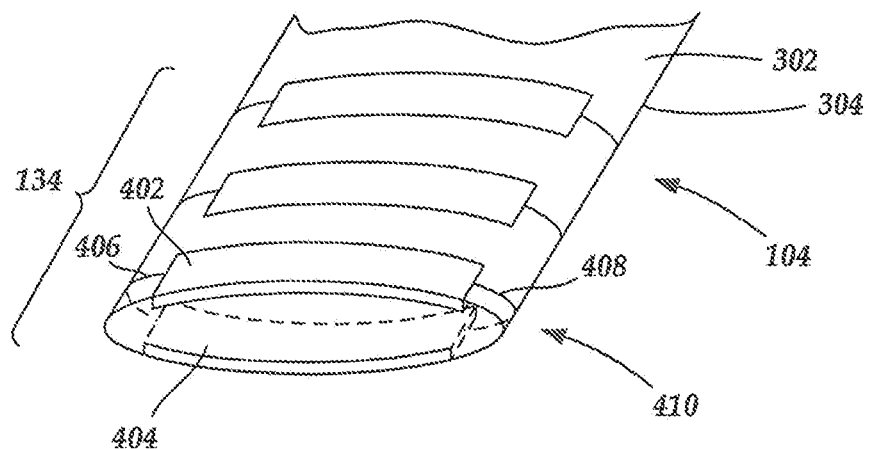
FIG. 4A is a schematic cross-sectional/perspective view of another embodiment of a paddle body for use in an electrical stimulation system, according to the invention.

FIG. 4A is a schematic cross-sectional/perspective view of another embodiment of a paddle body for use in an electrical stimulation system, according to the invention. In FIG. 4A, a first electrode 402 disposed on the anterior surface 302 is electrically coupled to a second electrode 404 disposed on the inferior surface 304 by peripheral connecting wires 406 and 408 extending laterally around the surface of the paddle body 104. The peripheral connecting wires 406 and 408 are each disposed on both the anterior surface 302 and the inferior surface 304 of the paddle body 104. Collectively, the first electrode 402, the second electrode 404, and the two peripheral connecting wires 406 and 408 form a coupled arrangement 410. An electrode array 134 includes a number of similar laterally-extending coupled arrangements disposed along a longitudinal axis of the paddle body 104.

An electrode in a coupled arrangement has a cross-sectional area that is much larger in size than a coupled peripheral connecting wire in the coupled arrangement. The cross-sectional area of an electrode in a coupled arrangement can be larger than the cross-sectional area of a peripheral connecting wire by different amounts. For example, an electrode can have a cross-sectional area that is at least two times larger than the cross-sectional of a peripheral connecting wire, at least five times larger than the cross-sectional area of a peripheral connecting wire, at least ten times larger than the cross-sectional area of a peripheral connecting wire, at least fifteen times larger than the cross-sectional area of a peripheral connecting wire, at least twenty times larger than the cross-sectional area of a peripheral connecting wire, at least fifty times larger than the cross-sectional area of a peripheral connecting wire, at least one hundred times larger than the cross-sectional area of a peripheral connecting wire, or the cross-sectional area of an electrode in a coupled arrangement can be larger than the cross-sectional area of a peripheral connecting wire by larger amounts. As will be recognized, other relative cross-sectional areas may also be used.

The electrodes and peripheral connecting wires may be fabricated from any of a number of suitable conductive materials that are either flexible or nonflexible, including metals, alloys, conductive polymers, conductive carbon, and the like, as well as combinations thereof. The conductive materials used to fabricate the electrodes and the peripheral connecting wire may be the same or different.

Figure 4B:
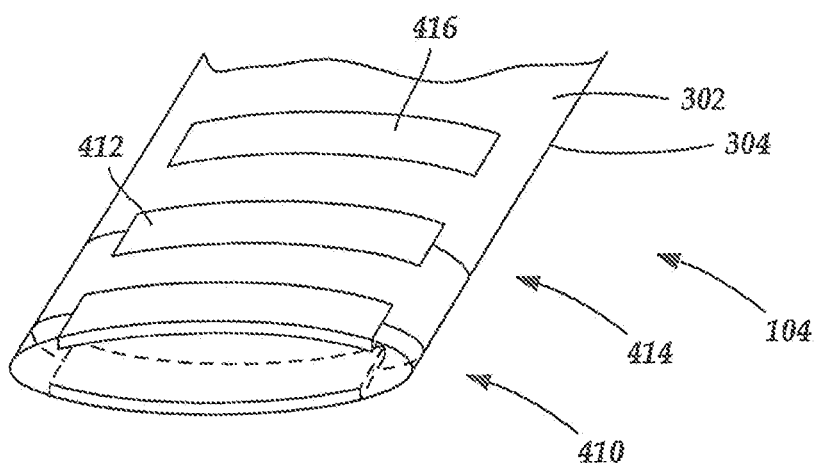
FIG. 4B is a schematic cross-sectional/perspective view of the embodiment of the paddle body shown in FIG. 4A with electrodes in both coupled arrangements and non-coupled arrangements for use in an electrical stimulation system, according to the invention.

A paddle body may contain an electrode array that includes one or more coupled arrangements and one or more electrodes that do not form a coupled arrangement. FIG. 4B is a schematic cross-sectional/perspective view of the embodiment of the paddle body shown in FIG. 4A with electrodes in both coupled arrangements and non-coupled arrangements for use in an electrical stimulation system, according to the invention. In FIG. 4B, the coupled arrangement 410 extends laterally around the periphery of paddle body 104. Likewise, coupled arrangement 414 includes a third electrode 412 disposed on the anterior surface, a fourth electrode (not shown in FIG. 4B) disposed on the inferior side 304, and two peripheral connecting wires electrically coupling the third electrode and the fourth electrode. However, the paddle body 104 also includes a fifth electrode 416 disposed on the anterior side 302 that is not coupled to a corresponding electrode on the inferior side 304.

Figure 5A:
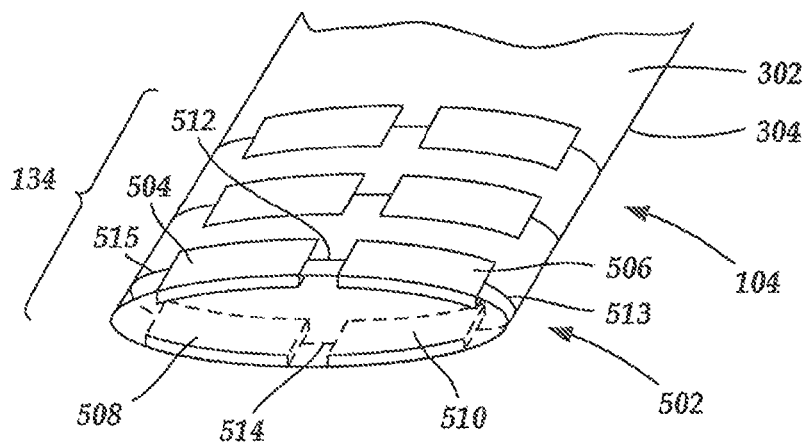
FIG. 5A is a schematic cross-sectional/perspective view of a third embodiment of a paddle body for use in an electrical stimulation system, according to the invention.

A coupled arrangement may use additional electrodes and connecting wires to extend laterally around the periphery of a paddle body. FIG. 5A is a schematic cross-sectional/perspective view of a third embodiment of a paddle body for use in an electrical stimulation system, according to the invention. In FIG. 5A, a coupled arrangement 502 includes two electrodes 504 and 506 on the anterior surface 302, two electrodes 508 and 510 on the inferior surface 304, and peripheral connecting wires 512-515 electrically coupling each of the four electrodes 504, 506, 508, and 510 and extending laterally around the periphery of the paddle body 104. A number of similar laterally-extending coupled arrangements disposed along a longitudinal axis of the paddle body 104 create electrode array 134.

Figure 5B:
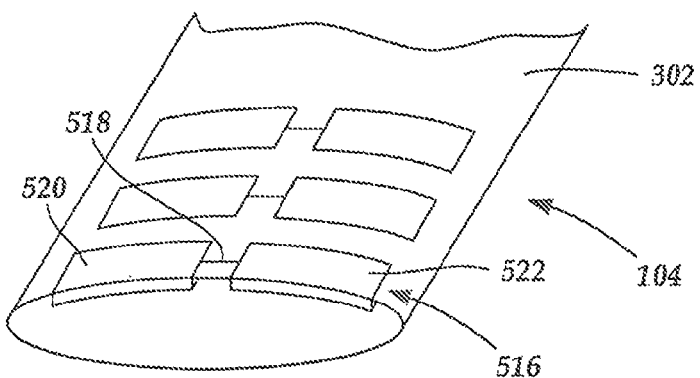
FIG. 5B is a schematic cross-sectional/perspective view of the paddle body shown in FIG. 5A with single-sided coupled arrangements for use in an electrical stimulation system, according to the invention.

A coupled arrangement may include two or more electrodes electrically coupled in a lateral direction by one or more peripheral connecting wires without forming a lateral loop. Additionally coupled arrangements can be disposed on either an anterior side or an inferior side of a paddle body without also being disposed on the opposing side. FIG. 5B is a schematic cross-sectional/perspective view of the paddle body shown in FIG. 5A with single-sided coupled arrangements for use in an electrical stimulation system, according to the invention. In FIG. 5B, a coupled arrangement 516 is disposed on the anterior surface 302 of the paddle body 104 and includes a peripheral connecting wire 518 electrically coupling a first electrode 520 and a second electrode 522. In other embodiments, a coupled arrangement is disposed laterally on an inferior surface of a paddle body. In yet other embodiments, a coupled arrangement is disposed laterally on both an anterior and an inferior surface without forming a lateral loop.

Figure 6:
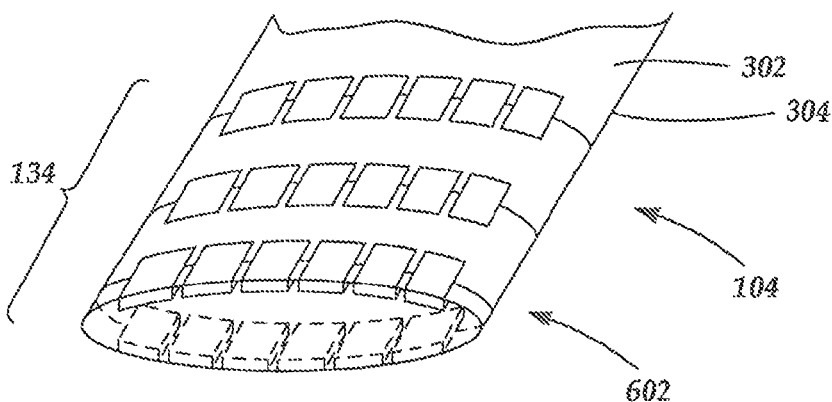
FIG. 6 is a schematic cross-sectional/perspective view of a fourth embodiment of a paddle body for use in an electrical stimulation system, according to the invention.

FIG. 6 is a schematic cross-sectional/perspective view of a fourth embodiment of a paddle body for use in an electrical stimulation system, according to the invention. In FIG. 6, a coupled arrangement 602 includes six electrodes on the anterior surface 302, six electrodes on the inferior surface 304, and twelve peripheral connecting wires electrically coupling each of the twelve electrodes and extending laterally around the periphery of the paddle body 104. A number of similar laterally-extending coupled arrangements disposed along a longitudinal axis of the paddle body 104 create electrode array 134.

A coupled arrangement may use additional electrodes and peripheral connecting wires to extend laterally around the surface of a paddle body. For example, there can be eight electrodes and sixteen peripheral connecting wires, ten electrodes and twenty peripheral connecting wires, twelve electrodes and peripheral twenty-four connecting wires, sixteen electrodes and thirty-two peripheral connecting wires, or more electrodes and peripheral connecting wires. As will be recognized, other numbers of electrodes and peripheral connecting wires may also be used.

Similarly, an electrode array may include variable numbers of longitudinally-spaced coupled arrangements. For example, there can be one, two, three, four, five, six, seven, eight, nine, ten, twelve, fourteen, sixteen, twenty, twenty-four, twenty-eight, thirty-two, thirty-six, or more longitudinally-spaced coupled arrangements. As will be recognized, other numbers of coupled arrangements may also be used. Additionally, the number of coupled arrangements disposed along a longitudinal axis of the paddle body 104 create electrode array 134.

As shown in FIGS. 3-6, multidirectional stimulation may be achieved using one or more coupled arrangements extending around the periphery of a paddle body. In alternate embodiments of the present invention, multidirectional stimulation may be achieved using coupled arrangements that include a number of electrodes on an anterior surface of a paddle body electrically coupled to a number of electrodes on an inferior surface of the paddle body by transverse connecting wires that pass through the interior of the paddle body.

Figure 7A:
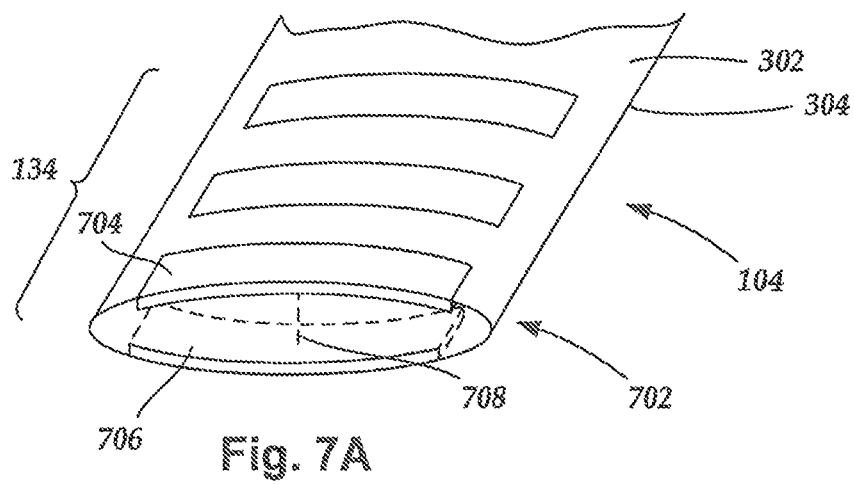
FIG. 7A is a schematic cross-sectional/perspective view of a fifth embodiment of a paddle body for use in an electrical stimulation system, according to the invention.

FIG. 7A is a schematic cross-sectional/perspective view of a fifth embodiment of a paddle body for use in an electrical stimulation system, according to the invention. In FIG. 7A, a coupled arrangement 702 includes an anterior electrode 704 disposed on anterior surface 302 electrically coupled to an inferior electrode 706 disposed on inferior surface 304 by a transverse connecting wire 708 that extends transversely through the paddle body 104. As discussed above, with reference to FIG. 4A, the electrodes have a much larger surface area than the transverse connecting wires and both the electrodes and the transverse connecting wires may be fabricated from any of a number of suitable conductive materials that are either flexible or nonflexible, including metals, alloys, conductive polymers, conductive carbon, and the like, as well as combinations thereof. The conductive materials used to fabricate the electrodes and transverse connecting wires may be the same or different.

Figure 7B:
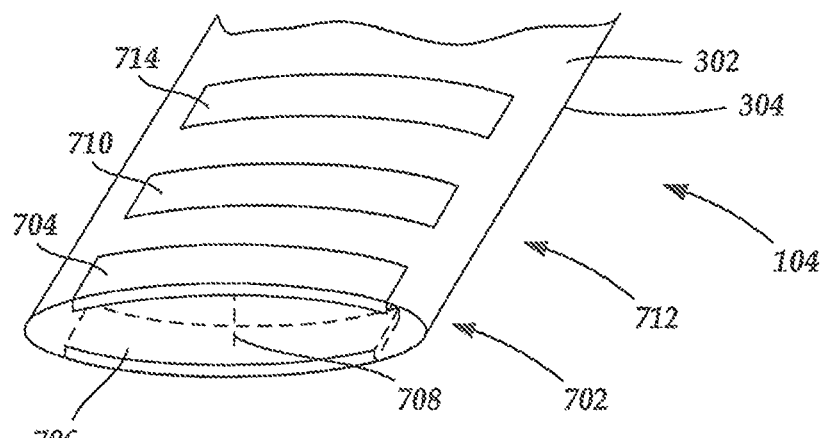
FIG. 7B is a schematic cross-sectional/perspective view of the embodiment of the paddle body shown in FIG. 7A with electrodes in both coupled arrangements and non-coupled arrangements for use in an electrical stimulation system, according to the invention.

A paddle body may contain an electrode array that includes one or more transversely-interconnected coupled arrangements and one or more electrodes that do not form a coupled arrangement. FIG. 7B is a schematic cross-sectional/perspective view of the embodiment of the paddle body shown in FIG. 7A with electrodes in both coupled arrangements and non-coupled arrangements for use in an electrical stimulation system, according to the invention. In FIG. 7B, the coupled arrangement 702 extends transversely through paddle body 104. Likewise, a third electrode 710 disposed on the anterior surface 302 also forms a coupled arrangement 712, together with a fourth electrode (not shown in FIG. 7B) disposed on the inferior side 304 and the corresponding transverse connecting wire. However, the paddle body 104 also includes a fifth electrode 714 disposed on the anterior side 302 that is not coupled to a corresponding electrode on the inferior side 304.

Figure 8:
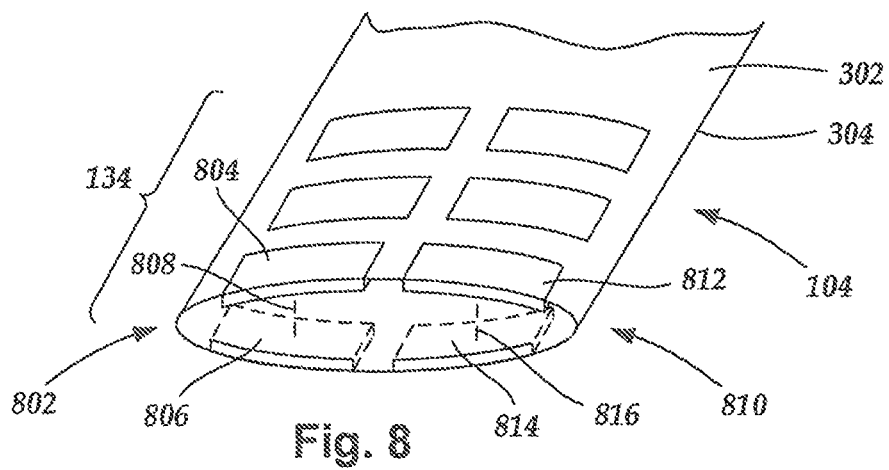
FIG. 8 is a schematic cross-sectional/perspective view of a sixth embodiment of a paddle body for use in an electrical stimulation system, according to the invention.

FIG. 8 is a schematic cross-sectional/perspective view of a sixth embodiment of a paddle body for use in an electrical stimulation system, according to the invention. In FIG. 8, a first coupled arrangement 802 includes an anterior electrode 804 on the anterior surface 302 electrically coupled with an inferior electrode 806 on the inferior surface 304 by transverse connecting wire 808. Similarly, a second coupled arrangement 810 includes an anterior electrode 812, positioned adjacent along a lateral axis from anterior electrode 804, is electronically coupled to an inferior electrode 814, positioned adjacent along a lateral axis from anterior electrode 806, by a transverse connecting wire 816. A number of similar pairs of coupled arrangements disposed along a longitudinal axis of the paddle body 104 create electrode array 134.

Figure 9:
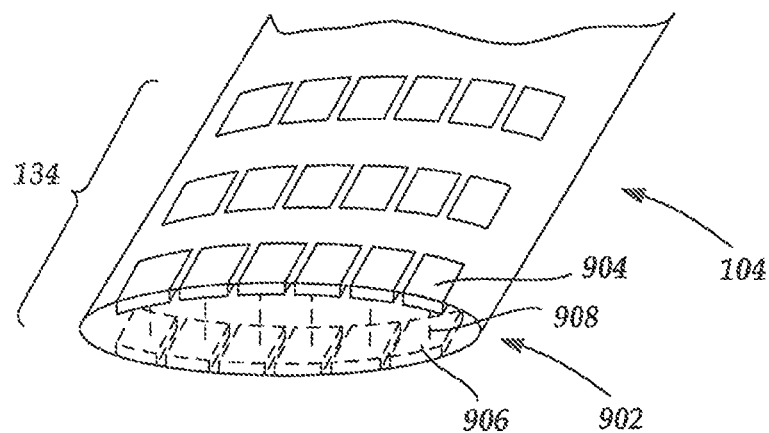
FIG. 9 is a schematic cross-sectional/perspective view of a seventh embodiment of a paddle body for use in an electrical stimulation system, according to the invention.

FIG. 9 is a schematic cross-sectional/perspective view of a seventh embodiment of a paddle body for use in an electrical stimulation system, according to the invention. In FIG. 9, six coupled arrangements, such as coupled arrangement 902, include one of six laterally-spaced anterior electrodes, such as anterior electrode 904, coupled electronically to one of six laterally-spaced inferior electrodes opposite to the six laterally-spaced anterior electrodes, such as inferior electrode 906, by one of six transverse connecting wires, such as transverse connecting wire 908. A number of similar coupled arrangements disposed along a longitudinal axis of the paddle body 104 create electrode array 134.

Figure 10A:
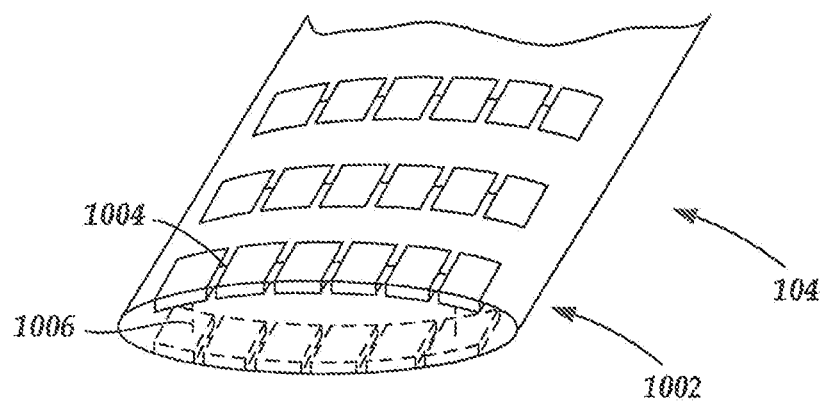
FIG. 10A is a schematic cross-sectional/perspective view of an embodiment of a coupled arrangement forming a lateral loop on a paddle body for use in an electrical stimulation system, according to the invention.

Coupled arrangements can be created with both peripheral connecting wires and transverse connecting wires to form a lateral loop in a paddle body. FIG. 10A is a schematic cross-sectional/perspective view of an embodiment of a coupled arrangement forming a lateral loop on a paddle body for use in an electrical stimulation system, according to the invention. In FIG. 10A, a coupled arrangement 1002 forming a lateral loop in a paddle body 104 includes ten peripheral connecting wires, such as peripheral connecting wire 1004, and two transverse connecting wires, such as transverse connecting wire 1006.

Figure 10B:
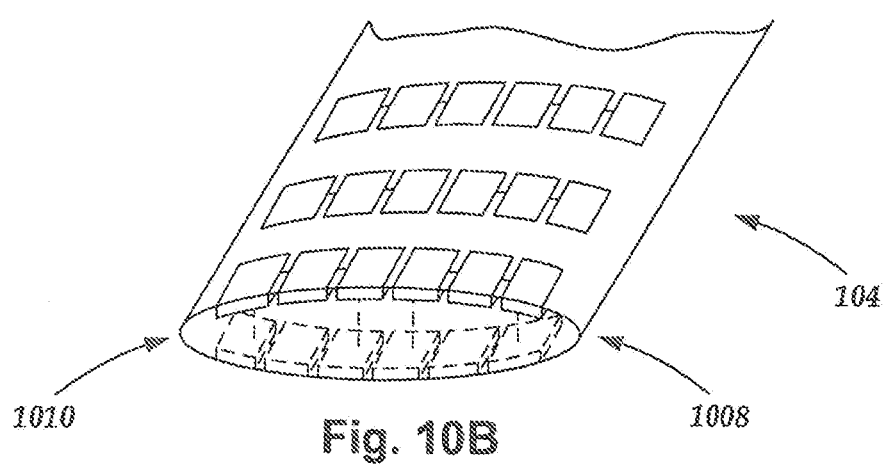
FIG. 10B is a schematic cross-sectional/perspective view of an embodiment of a coupled arrangement forming two lateral loops on a paddle body for use in an electrical stimulation system, according to the invention.
Figure 10C:
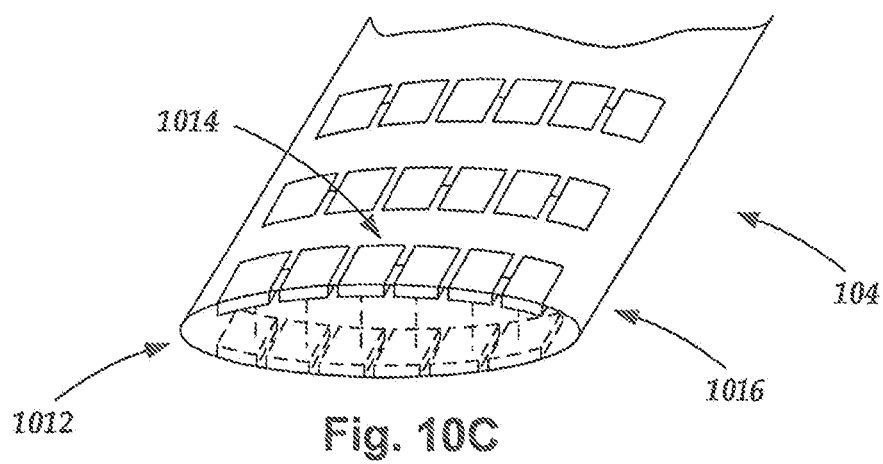
FIG. 10C is a schematic cross-sectional/perspective view of an embodiment of a coupled arrangement forming three lateral loops on a paddle body for use in an electrical stimulation system, according to the invention.

Additional laterally-spaced lateral loops can be created in a paddle body by using more coupled arrangements with fewer electrodes and connecting wires. FIG. 10B is a schematic cross-sectional/perspective view of an embodiment of a coupled arrangement forming two lateral loops on a paddle body for use in an electrical stimulation system, according to the invention. In FIG. 10B, each of two laterally-spaced coupled arrangements 1008 and 1010 form a lateral loop in a paddle body 104 using both peripheral connecting wires and transverse connecting wires. FIG. 10C is a schematic cross-sectional/perspective view of an embodiment of coupled arrangements forming three lateral loops on a paddle body for use in an electrical stimulation system, according to the invention. In FIG. 10C, each of three laterally-spaced coupled arrangements 1012, 1014, and 1016 form a lateral loop in a paddle body 104 using both peripheral connecting wires and transverse connecting wires.

Figure 11:
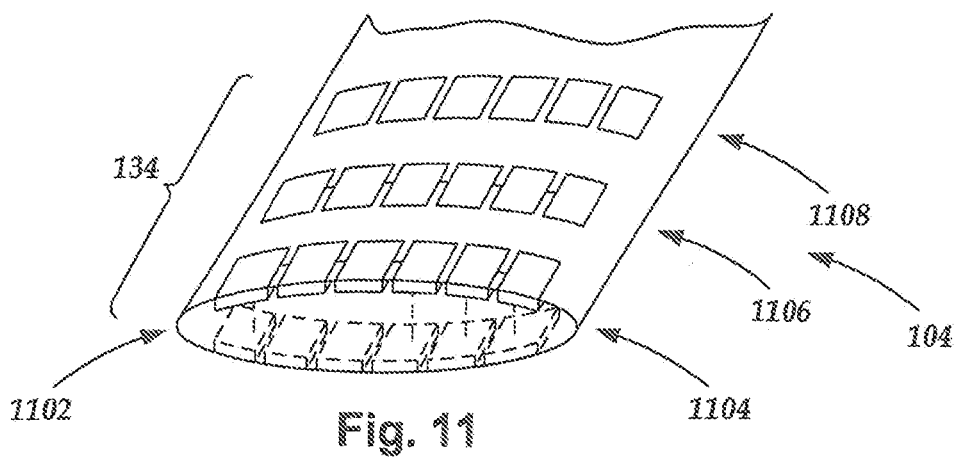
FIG. 11 is a schematic cross-sectional/perspective view of an embodiment of a paddle body with various coupled arrangements and non-coupled arrangements for use in an electrical stimulation system, according to the invention.

An electrode array can include various combinations of coupled and non-coupled arrangements either with or without using one or more lateral loops of either uniform or non-uniform sizes electrically coupled with peripheral connecting wires and/or transverse connecting wires. FIG. 11 is a schematic view of an embodiment of a paddle body with various coupled arrangements and non-coupled arrangements for use in an electrical stimulation system, according to the invention. In FIG. 11, the electrode array 134 includes two differently-sized coupled arrangements 1102 and 1104 forming lateral loops, one coupled arrangement 1106 with electrodes disposed only on the anterior surface 302, and six non-coupled electrodes 1108. In various other embodiments, different combinations of coupled and non-coupled arrangements either with or without using one or more lateral loops of either uniform or non-uniform sizes electrically coupled with peripheral connecting wires and/or transverse connecting wires can be utilized in an electrode array on a paddle body.

Appropriate electrically-coupled electrodes can be selected to stimulate a desired tissue region. For example, selection of the electrodes to provide electrical stimulation can be made by experimentation to determine which electrodes best stimulate the desired tissue. Various combinations of electrodes may be tested, for example, with a patient providing responses regarding the effects of stimulation of each particular combination of electrodes or the effect of the electrical stimulation can be observed instrumentally and/or visually. Note that an electrode configuration on a paddle body that includes both peripherally and transversely coupled electrodes can provide a vast number of possible simultaneous stimulation locations.

It should be apparent that increasing the number of electrodes disposed laterally around the circumference of a paddle body increases the flexibility of a paddle lead when the materials used to fabricate the paddle body are more flexible than the materials used to fabricate the electrodes. Additional methods of increasing flexibility may also be used in tandem with the embodiments described above, including use of flexible materials and reducing the size of one or more electrodes disposed on a paddle lead.

Figure 12:
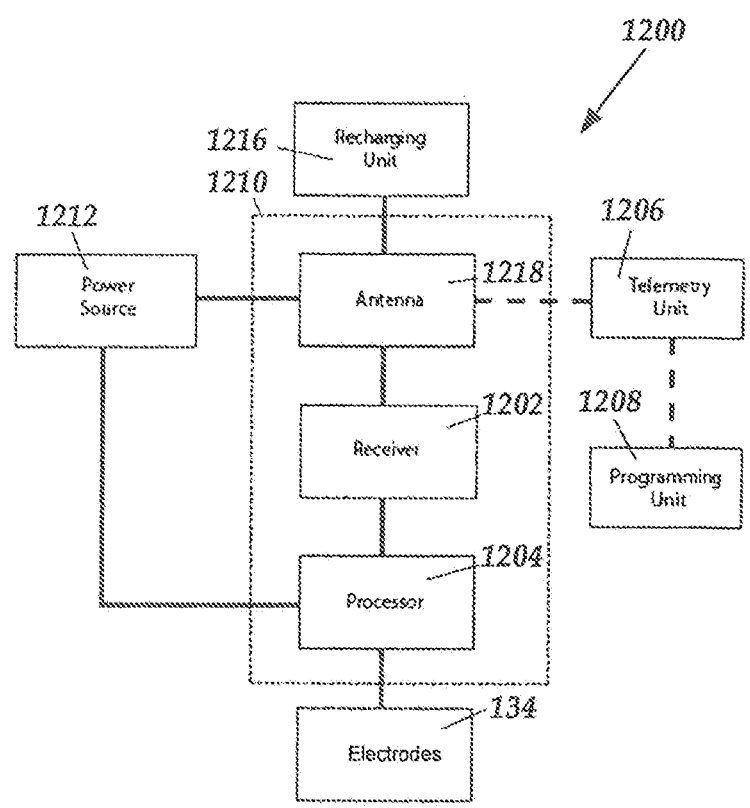
FIG. 12 is a schematic overview of one embodiment of components of a stimulation system 1200 including an electronic subassembly 1210 disposed within a control module.

FIG. 12 is a schematic overview of one embodiment of components of a stimulation system 1200 including an electronic subassembly 1210 disposed within a control module. It will be understood that the stimulation system can include more, fewer, or different components and can have a variety of different configurations including those configurations disclosed in the stimulator references cited herein.

Some of the components (for example, power source 1212, antenna 1218, receiver 1202, and processor 1204) of the stimulation system can be positioned on one or more circuit boards or similar carriers within a housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above.

In one embodiment, electrical current is emitted by the electrodes 134 on the paddle or lead body to stimulate nerve fibers, muscle fibers, or other body tissues near the stimulation system. A processor 1204 is generally included to control the timing and electrical characteristics of the stimulation system. For example, the processor can, if desired, control one or more of the timing, frequency, strength, duration, and waveform of the pulses. In addition, the processor 1204 can select which electrodes can be used to provide stimulation, if desired. In some embodiments, the processor may select which electrode(s) are cathodes and which electrode(s) are anodes. In some embodiments, the processor may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allow modification of pulse characteristics. In the illustrated embodiment, the processor 1204 is coupled to a receiver 1202 which, in turn, is coupled to the optional antenna 1218. This allows the processor to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by a programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit may not be worn or carried by the user but may only be available at a home station or at a clinician's office. The programming unit 1208 can be any unit that can provide information to the telemetry unit for transmission to the stimulation system. The programming unit 1208 can be part of the telemetry unit 1206 or can provide signals or information to the telemetry unit via a wireless or wired connection. One example of a suitable programming unit is a computer operated by the user or clinician to send signals to the telemetry unit.

The signals sent to the processor 1204 via the antenna 1218 and receiver 1202 can be used to modify or otherwise direct the operation of the stimulation system. For example, the signals may be used to modify the pulses of the stimulation system such as modifying one or more of pulse duration, pulse frequency, pulse waveform, and pulse strength. The signals may also direct the stimulation system to cease operation, to start operation, to start charging the battery, or to stop charging the battery. In other embodiments, the stimulation system does not include an antenna 1218 or receiver 1202 and the processor 1204 operates as programmed.

Optionally, the stimulation system may include a transmitter (not shown) coupled to the processor and antenna for transmitting signals back to the telemetry unit 1206 or another unit capable of receiving the signals. For example, the stimulation system may transmit signals indicating whether the stimulation system is operating properly or not or indicating when the battery needs to be charged or the level of charge in the battery. The processor may also be capable of transmitting information about the pulse characteristics so that a user or clinician can determine or verify the characteristics.

A paddle body may be formed in the desired shape by any number of processes including, for example, molding (including injection molding), casting, and the like. Electrodes and connecting wires can be disposed onto or within a paddle body either prior to or subsequent to a molding or casting process.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected under United States Letters Patent is:

1. A paddle lead, comprising:
    a paddle body having a first major surface, an opposing second major surface, and a transverse circumference;
    a plurality of electrodes disposed on the paddle body, the plurality of electrodes comprising a first electrode and a second electrode, the first electrode and the second electrode being disposed laterally around the transverse circumference of the paddle body; and
    a first connecting wire disposed on at least one of the first and second major surfaces of the paddle body to electrically couple the first electrode and the second electrode.

2. The paddle lead of claim 1, wherein the first electrode is disposed on the first major surface, the second electrode is disposed on the second major surface, and the first connecting wire is disposed on both the first and second major surfaces.

3. The paddle lead of claim 1, wherein the first and second electrodes are both disposed on the first major surface.

4. The paddle lead of claim 3, wherein the plurality of electrodes further comprises a third electrode and a fourth electrode, the third and fourth electrodes being disposed laterally around the transverse circumference of the paddle body, the paddle lead further comprising a second connecting wire disposed on at least one of the first and second major surfaces of the paddle body to electrically couple the third electrode and the fourth electrode.

5. The paddle lead of claim 4, wherein the first, second, third, and fourth electrodes are disposed laterally around the transverse circumference of the paddle body, the paddle lead further comprising a third connecting wire disposed on at least one of the first and second major surfaces of the paddle body to electrically couple the third electrode and the second electrode.

6. The paddle lead of claim 5, wherein the third and fourth electrodes are disposed on the second major surface.

7. The paddle lead of claim 5, wherein the third and fourth electrodes are disposed on the first major surface.

8. The paddle lead of claim 5, wherein the third electrode is disposed on the first major surface and the fourth electrode is disposed on the second major surface.

9. The paddle lead of claim 5, further comprising a fourth connecting wire disposed on at least one of the first and second major surfaces of the paddle body to electrically couple the fourth electrode and the first electrode.

10. The paddle lead of claim 4, wherein the first, second, third, and fourth electrodes are disposed laterally around the transverse circumference of the paddle body and the third and fourth electrodes are disposed on the second major surface, the paddle lead further comprising a third connecting wire disposed within the paddle body to electrically couple the third electrode and the second electrode.

11. The paddle lead of claim 10, wherein further comprising a fourth connecting wire disposed within the paddle body to electrically couple the fourth electrode and the first electrode.

12. The paddle lead of claim 4, wherein the third and fourth electrodes are disposed on the first major surface.

13. A stimulation system, comprising:
    the paddle lead of claim 1; and
    a control module coupleable to the paddle lead.

14. A paddle lead, comprising:
    a paddle body having a first major surface, an opposing second major surface, and a transverse circumference;
    a plurality of electrodes disposed on the paddle body, the plurality of electrodes comprising a plurality of first electrodes disposed on the first major surface and a plurality of second electrodes disposed on the second major surface, the first electrodes and the second electrodes being disposed laterally around the transverse circumference of the paddle body; and
    a plurality of first connecting wires disposed on the first major surface of the paddle body to electrically couple the plurality of first electrodes together.

15. The paddle lead of claim 14, further comprising a plurality of second connecting wires disposed on the second major surface of the paddle body to electrically couple the plurality of second electrodes together.

16. The paddle lead of claim 15, further comprising at least one third connector wire disposed on the first and second major surfaces of the paddle body to electrically couple the plurality of first electrodes to the plurality of second electrodes.

17. The paddle lead of claim 15, further comprising at least one third connector wire disposed within the paddle body to electrically couple the plurality of first electrodes to the plurality of second electrodes.

18. The paddle lead of claim 14, wherein the plurality of electrodes further comprises a plurality of third electrodes disposed on the first major surface and a plurality of fourth electrodes disposed on the second major surface, the third electrodes and the fourth electrodes being disposed laterally around the transverse circumference of the paddle body, the third and fourth electrodes being disposed longitudinally spaced apart from the first and second electrodes.

19. The paddle lead of claim 18, further comprising a plurality of third connecting wires disposed on the first major surface of the paddle body to electrically couple the plurality of third electrodes together and a plurality of fourth connecting wires disposed on the second major surface of the paddle body to electrically couple the plurality of fourth electrodes together.

20. A stimulation system, comprising:
    the paddle lead of claim 14; and
    a control module coupleable to the paddle lead.

* * * * *